US00PP35864P2

(12) United States Plant Patent
McKittrick

(10) Patent No.: US PP35,864 P2
(45) Date of Patent: Jun. 11, 2024

(54) BOXWOOD PLANT NAMED 'CLAIR OLIVER'

(50) Latin Name: *Buxus sempervirens*
Varietal Denomination: Clair Oliver

(71) Applicant: Hugh McKittrick, Colts Neck, NJ (US)

(72) Inventor: Hugh McKittrick, Colts Neck, NJ (US)

( * ) Notice: Subject to any disclaimer, the term of this patent is extended or adjusted under 35 U.S.C. 154(b) by 0 days.

(21) Appl. No.: 18/445,179

(22) Filed: May 12, 2023

(51) Int. Cl.
*A01H 5/12* (2018.01)
*A01H 6/00* (2018.01)

(52) U.S. Cl.
USPC ..... Plt./226

(58) Field of Classification Search
USPC ..... Plt./226
CPC ..... A01H 5/12; A01H 5/00; A01H 6/00
See application file for complete search history.

(56) References Cited

U.S. PATENT DOCUMENTS

PP32,309 P2 * 10/2020 Hermans ..... A01H 6/00 Plt./226
PP32,421 P2 * 11/2020 Saunders ..... A01H 6/00 Plt./226
2016/0381845 P1 * 12/2016 McKittrick ..... A01H 6/00 800/298

* cited by examiner

*Primary Examiner* — June Hwu

(57) ABSTRACT

A New and distinct *Buxus sempervirens* (Boxwood) cultivar of benefit to the Ornamental plant industry. This Boxwood shall here forth be known as 'Clair Oliver'. The plant has a definite upright pyramidal form with 1 (one) central leader, with a radiating branch structure consisting of widely spaced internodes in an alternating pattern. The leaves are noticeably large. The coloration on large, newly emerged leaves possesses an opalescence. The adult foliage possesses a stable dark green color throughout the year. These traits have been observed over the past several winters to have survived temperatures of −1 (minus one) degrees Fahrenheit in an outdoor, exposed site. Fragrance has not been observed in any season or condition. These traits were maintained throughout three generations of asexual propagation by rooted cutting.

2 Drawing Sheets

Figure 1:
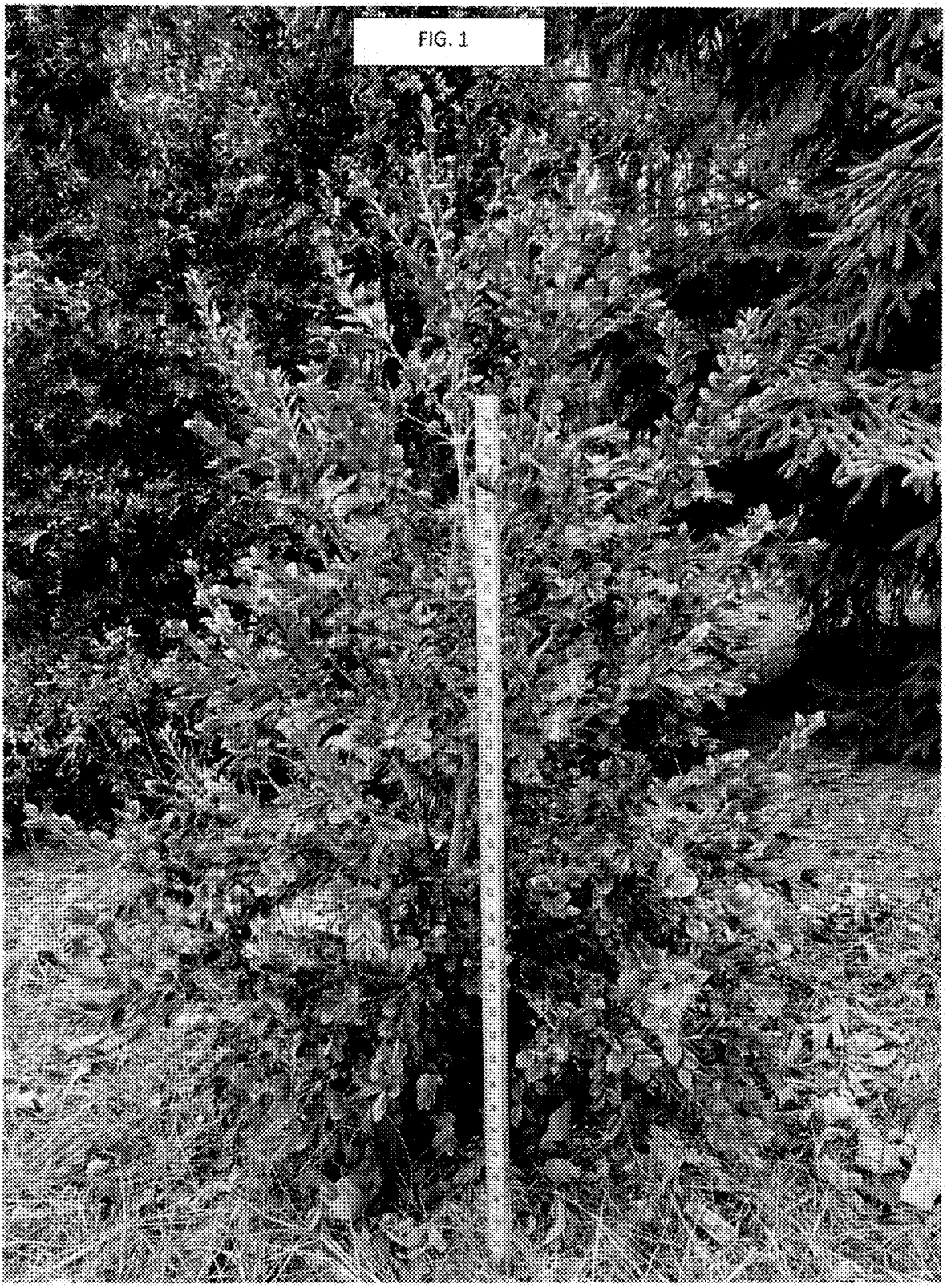

(d.) Latin name of plant claimed: *Buxus sempervirens.*
(e.) Variety denomination: 'Clair Oliver'.

(b.) CROSS-REFERENCE TO RELATED APPLICATIONS

Nonapplicable.

(c.) FEDERALLY SPONSORED RESEARCH & DEVELOPMENT

This invention nor any related activities leading to it were associated with, or the product of, federally sponsored research.

(f.) BACKGROUND OF THE INVENTION

The continued preservation and subsequent use of this plant will benefit the ornamental plant industry by offering a unique, visually appealing plant with greater cold tolerance than existing varieties.

This new cultivar possesses naturally occurring qualities that distinguish it from related cultivars. Growth rate is faster, Narrow pyramidal in form, with a natural central leader, uniform radial horizontal branching. This feature has naturally survived and retained form in all observed snow loads. The adult foliage color reflects parentage of *Buxus*

*sempervirens*, 'Clair Curtis'. Differing with all others with uniquely newly emerging foliage possessing a noticeable blue matte opalescent on the top surface of the leaf. Adult and juvenile plant characteristics, darker leaf color and leaf shape of a larger measured size of 30 mm in length, and with a shape that is elliptical with rounded base. The growth rate of 8 (eight) foot tall at 10 years with 1 (one) central leader. The plant at 10 (years) measuring at base of 3.5 (three and a half feet) and height of 8 (eight) feet. The growth habit is an upright pyramid of a loose and open course texture radiating from a central leader. are substantially in contrast to the Non patented plant 'Clair Curtis' in rate of growth. The new invention attaining an obvious greater height at 10 years 8 (eight) foot tall plant, While the parent 'Clair Curtis' attained a height of 6 (six) foot tall in 10 (ten) years. Results of plants being grown in same location to keep phenology replicated. Leaf coloration of 'Clair Oliver' emerging upper surface color of 110D (very light blue) with 131A (dark bluish green) and 131A summer leaf color.

Different from plant U.S. Plant Pat. No. 32,421 P2. *Buxus* plant named 'SB300'. The plant 'SB300' being a tight, upright, and very compact plant habit. Leaf color, in contrast with young leaf's; upper and lower surface 144A, mature leaves; upper surface NN137A, lower surface 144A. leaf size in contrast measuring up to an average of 2 cm in length and 1.7 cm in width. The growth habit is broader at the base than *Buxus sempervirens* 'Dee Runk' or *Buxus sempervirens*

'Pyramidalis' (both plants non-patented) and is distinctly different in most other characteristics, Both plants 'Dee Runk' and 'Pyramidalis' leaf length is similar to new invention, the leaf in contrast is half the width of new invention Both 'Dee Runk' and 'Pyramidalis' Leaf color of mature 1 (one) year old plants is a noticeably darker green, Leaf shape of both of these plants are lanceolate as in contrast to the new Inventions leaf's more elliptical. Both 'Dee Runk' and 'Pyramidalis' Both have multi upright stem trunks in contrast to The new invention having a single main trunk. Neither of these plants have a central leader or possess opalescence of newly emerged growth.

This newly discovered plant 'Clair Oliver' Foliage coloration and quality has been retained, while withstanding −1 (minus one degrees) Fahrenheit. Since the 2006 discovery of this plant, it has exhibited a natural resistance to pests commonly associated with the *Buxus sempervirens*. The rate of growth, has been reliably 9 (nine) inches annually and, resulting in an 8' (eight foot) in height. This invention differs from the previously patented *Buxus sempervirens* 'HER2010B02' (U.S. Plant Pat. No. 32,309 P2) and in coloration of immature upper surface leaf color of 143A (strong yellow green) to 144A (strong yellow green) and mature upper surface leaf color between NN137A (grayish olive green). contrasting leaf size of an average of 1.8 cm in length and 1.0 cm in width. Growth. In Contrast to *Buxus* 'Sky Walker' (U.S. Plant Pat. No. 22,977) distinguishable by its more columnar than Pyramidal. The contrasting rate of growth attaining 1.8 m (6 feet) in height and 30 to 38 cm (12-15 inches) in width in 6 years. Leaf size an average of 3.5 cm in length and 2 cm in width when mature. Leaf coloration; newly expanded leaves; upper surface a blend of 144A and 144B, lower surface; 144B, mature leaves; upper surface N137A, lower surface a blend of 138A and 144A.

The combination of unique and meritorious features of this plant indicates its use as a specimen or hedge planting. The ornamental qualities of this newly discovered plant provide visual interest. This plant has expressed attractive traits exhibited as a coarse and rugged textural quality. Juvenile leaf growth possesses a blue opalescence persisting into the hardening off stage of development. The large evergreen leaves, in opposing sets, on widely spaced internodes arranged in a mildly alternating pattern of approximately 20 degrees from adjacent internodes. The strong annual growth rate allows for a multitude of applications. Superior performance in snow load conditions has been observed over several growing seasons. The plant has resisted 'Boxwood Blight' (*Calonectria pseudonaviculata*) while being grown in an open and unaltered block. This new cultivar will be of beneficial use and possess traits with widespread benefits to the ornamental plant industry.

(g.) SUMMARY OF THE INVENTION

This current invention relates to a new and distinct *Buxus sempervirens* cultivar that was discovered and selected in an area of a cultivated block the plant 'Clair Curtis' (U.S. Plant patent application Ser. No. 15/998,387, abandon) of nursery grown plants in AD 2006, located in Colts Neck, New Jersey; occurring as a natural branch mutation of *Buxus sempervirens* 'Clair Curtis'. Successful asexual reproduction was conducted and repeated in Colts Neck New Jersey from 2007 and thereafter. The method of asexual reproduction was by way of rooting cuttings within a greenhouse environment.

This hybrid exhibits distinctively different characteristics consistent with parentage of the non-patented plant *Buxus sempervirens* 'Clair Curtis' This one distinct plant has a collective list of characteristics that have been historically observed in various climatic and environmental conditions. The observations trials were conducted in a side by side comparison. These observations were common and consistent throughout test bock. The characteristics of this unique genotype appear to be specific and individual in nature. These observed and expressed distinctive combination of traits are described:

1. Pyramidal shape and a course, rugged branch structure.
2. Single main trunk structure.
3. Large leaves.
4. Opalescent juvenile foliage.
5. Results of reproduction from asexual cuttings are true.
6. Rate of growth in excess of parentage of 'Clair Curtis'.
7. Resistance to "Boxwood Blight" (*Calonectria pseudonaviculata*)
8. Deer and other animal damage not observed.

(h.) DESCRIPTION OF DRAWING

The accompanying color FIGURES shows this new plant for the purpose of general and specific observations. Colors in the photographs may be different than the written description. Photographs FIG. 1 and FIG. 2 both of 6-year-old plants.

Photograph, FIG. 1: Adult foliage shown late winter before new growth emergence. FIG. 1, of entire plant in observation site in Colts Neck, New Jersey.

Figure 2:
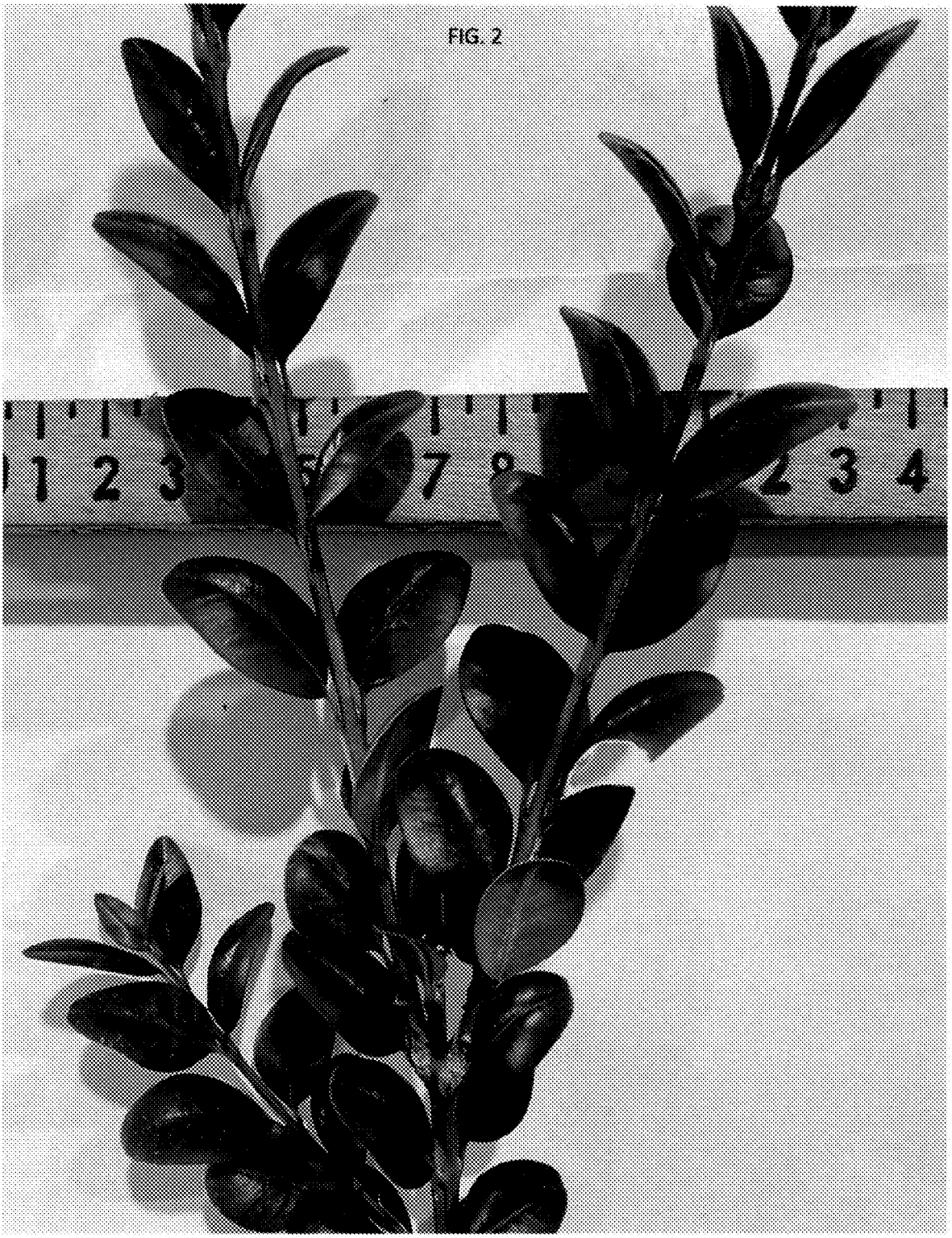

Photograph, FIG. 2: The cut portion of annual growth shown with ruler.

(i.) BOTANICAL DESCRIPTION

The subsequent description of the new plant is of a 2006 planting in Colts Neck, New Jersey. The details contained within have been repeatedly observed to have expressed these identifiable details. The colors referenced are standards set by The Royal Horticultural Society (R.H.S.) Colour Chart, 2015 edition, unless otherwise noted.

Type: Broad leafed, pyramidal shaped evergreen shrub for ornamental landscape use.

Botanical classification: *Buxus sempervirens* 'Clair Oliver'.

Growth habit: Medium growing, full bodied, course and rugged foliage and naturally forming pyramidal profile.

Dimensions: Measured at 10 (ten) years of age. Height: eight feet (8 feet), 243.84 cm.

Diameter: Base of three and a half feet (3.25 feet), 99.06 cm.

Propagation: Asexual method of rooted hardwood cuttings, in several, and varied trials. These trials re-produced the plant in a consistent and uniform manner. These reproductions have retained the unique and distinguishing characteristic traits of parent.

Leaf size: The one-year mature length average 30 mm. width average 20 mm. Shape: Elliptical with a rounded base and obtuse apices.

Margin: Entire.

Color: Upper leaf surface identified as 132A, with venation of 140B. Bottom surface 143C with venation of 144C, Juvenile leaf surface possessing an opalescent of 110D.

Arrangement: Opposite.

Branches: Diameter average of 8.0 mm., coarse bark texture, color 140A.

Size: Mature leaf one year growth length average 36 mm., width average 31 mm., Shape: Obcordate with rounded base and obcordate apices.

Margin: Entire.

Color: Upper leaf surface of newly emerged spring foliage possessing an obvious opalescent of 110D over a 131A green leaf. Summer: top foliage 131A. Winter: top foliage surface color 134A. Bottom foliage surface 144A. Venation upper surface 159A. Venation of bottom surface 162D.

Branches: Diameter average of 3.25 mm., coarse bark texture, color 146A,

Venation: Pinnate.

Petiole: 2.5 mm. medium light green in coloration.

Internodes: Average distance of 27 cm.

Inflorescence: Observed, mid may annually. Both male and female. Female with 6 sepals measuring 3 cm and male with 4 sepals measuring 3 cm., fragrance not detected, sepals basic white.

Fruit: Ovoid in shape, 3 valved 6 mm in length and 5 mm in width, coloration medium to dark green.

Diseases & pests: Untreated adult plant has been observed to resist commonly associated pests of Psyllid, leaf miner and Boxwood Blight (*Calonectria pseudonaviculata*).

Hardiness: U.S.D.A. zone 7A observed. Has survived −2 (minus two) degrees Fahrenheit without injury.

The invention claimed is:

1. A new and distinct variety of, Boxwood Plant named 'Clair Oliver', substantially as illustrated and described herein.

* * * * *